United States Patent [19]

Arnold et al.

[11] 4,038,320

[45] July 26, 1977

[54] PHENYLETHYNYL SUBSTITUTED AROMATIC DIAMINES

[75] Inventors: Fred E. Arnold, Centerville; Frederick L. Hedberg, Dayton, both of Ohio

[73] Assignee: The United States of America as represented by the Secretary of the Air Force, Washington, D.C.

[21] Appl. No.: 678,325

[22] Filed: Apr. 19, 1976

[51] Int. Cl.$^2$ .............................................. C07C 87/50
[52] U.S. Cl. ..................................... 260/578; 526/285
[58] Field of Search .......................... 260/578; 526/285

[56] References Cited

U.S. PATENT DOCUMENTS 3,928,450  12/1975  Bilow et al. .......................... 260/571
3,975,444   8/1976  Kovar et al. .......................... 260/571

FOREIGN PATENT DOCUMENTS 1,122,138  7/1968  United Kingdom

OTHER PUBLICATIONS

White et al., Chem. Ab. No. 116740d, vol. 67 (1967).
Mueller et al., Chem. Ab. No. 18892b, vol. 69 (1968).

*Primary Examiner*—Daniel E. Wyman
*Assistant Examiner*—J. Doll
*Attorney, Agent, or Firm*—Joseph E. Rusz; Cedric H. Kuhn

[57] ABSTRACT

As new compositions of matter, 2,2'-bis(phenylethynyl)-4,4'-diaminobiphenyl and 2,2'-bis(phenylethynyl)-5,5'-diaminobiphenyl. The compounds are useful as monomers suitable for the preparation of thermally stable polymer systems such as polyimides, polyamides and poly-Schiff bases.

3 Claims, No Drawings

PHENYLETHYNYL SUBSTITUTED AROMATIC DIAMINES

RIGHTS OF THE GOVERNMENT

The invention describes herein may be manufactured and used by or for the Government of the United States for all governmental purposes without the payment of any royalty.

FIELD OF THE INVENTION

This invention relates to phenylethynyl substituted aromatic diamine monomers. In one aspect the invention relates to the synhesis of the monomers.

BACKGROUND OF THE INVENTION

A number of polymeric systems have been investigated with the view of providing light-weight, high-temperature composites and adhesives for aircraft and aerospace structural applications. However, the matrix and adhesive resins that have been developed are subject to certain limitations. In general, the aliphatic systems have limited use temperatures because of their poor thermooxidative stability and moisture sensitivity. Although certain aromatic and aromatic-heterocyclic systems are moisture insensitive, they are limited by their poor processing parameters.

The principal processing problem inherent in a substantial number of aromatic and aromatic-heterocyclic systems is the absence of an effective method for curing the systems. High temperatures are necessary because extensive flow is mandatory for curing such resins by interchain chemical reactions. Because of their inherent rigidity, aromatic and aromatic-heterocyclic resins are much more susceptible to mobility dependence than are aliphatic resins. There is a need, therefore, for an entirely different method of cure which is not dependent upon extensive molecular mobility. Instead of systems that cure by interchain reactions, which require extensive mobility, improved systems are sought that cure by intramolecular reactions which require only rotational movement of the polymer backbone.

It is a principal object of this invention, therefore, to provide novel diamino aromatic monomers containing phenylethynyl pendant groups which cyclize and cure intramolecularly after polymerization. Other objects and advantages of the invention will become apparent to those skilled in the art upon consideration of the accompanying disclosure.

SUMMARY OF THE INVENTION

The present invention resides in biphenyl diamino compounds having the following formulas:

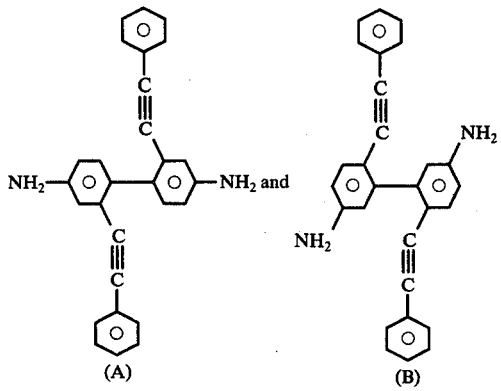

(A)                    (B)

As seen from the foregoing formulas, the amino groups are in either the 4,4' or 5,5' positions on the biphenyl ring system. In both compounds the 2,2' positions of the biphenyl ring system are substituted with phenylethynyl groups. After the monomers undergo condensation reactions with suitable comonomers, the pendant phenylethynyl groups along the polymer chains undergo intramolecular cycloaddition reactions, thereby providing a facile cure that is not dependent on excessive mobility. The monomers can be polymerized with conventional comonomers so as to prepare amide, urea, and Schiff base polymers. In particular, the monomers are useful in preparing imide type polymers by their condensation with aromatic tetracarboxylic acid dianhydrides, as disclosed in our copending U.S. application Ser. No. 678,324 filed on Apr. 19, 1976. The disclosure of this copending application is incorporated herein by reference.

The monomer represented by formula (A) above, i.e., 2,2'-bis(phenylethynyl)-4,4'-diaminobiphenyl, is synthesized by reacting copper phenylacetylide with 2,2'-diiodobenzidine in pyridine. The reaction involved can be represented by the following equation:

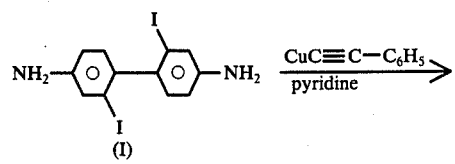

(I)

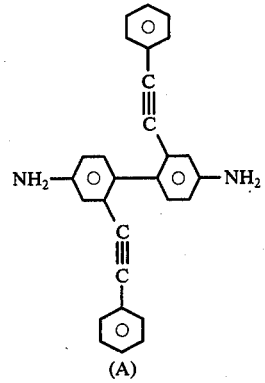

(A)

The monomer represented by formula (B) above, i.e., 2,2'-bis-(phenylethynyl)-5,5'-diaminobiphenyl, is prepared by a five-step reaction sequence. The reactions involved can be represented by the following equations:

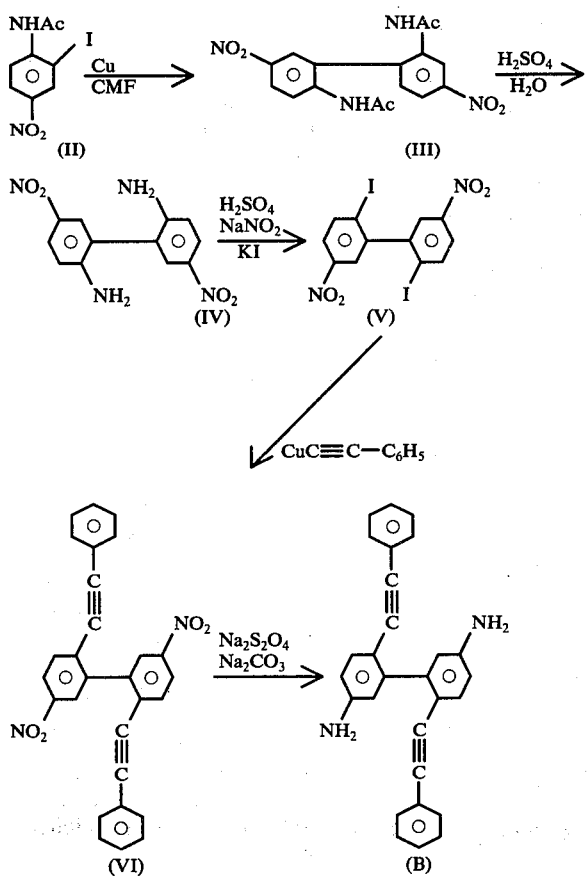

As shown by the above equations, initially 2-iodo-4:nitroacetanilide (II) is reacted with copper-bronze in dimethylformamide (DMF) to give 2,2'-bis(acetamido)-5,5'-dinitrobiphenyl (III). The acetamide groups of compound (III) are then hydrolyzed with sulfuric acid to give 2,2'-diamino-5,5'-dinitrobiphenyl (IV). Diazotisation of compound (IV) followed by reaction with potassium iodide in water gives 2,2'-diodo-5,5'-dinitrobiphenyl (V). Compound (V) is reacted with copper phenylacetylide to give 2,2'-bis(phenylethynyl)-5,5'-dinitrobiphenyl (VI). In the final step, compound (VI) is reduced with a solution of sodium dithionite and sodium carbonate in a water-dioxane mixture to give monomer B.

A more complete understanding of the invention can be obtained by referring to the following illustrative examples which are not intended, however, to be unduly limitative of the invention.

EXAMPLE I 2,2'-Bis(phenylethynyl)-4,4'-diaminobiphenyl (A)

A mixture of 2,2'-diiodobenzidine (8.8 g, 0.020 mole) and copper phenylacetylide (6.5 g, 0.040 mole) was stirred under a flow of dry nitrogen for 15 minutes, and then 250 ml of pyridine which had been simultaneously deaerated with dry nitrogen for 15 minutes was added. The reaction mixture was stirred and refluxed under nitrogen for 48 hours, during which time three 1.0 g (0.0061 mole) portions of copper phenylacetylide were added at 8, 24, and 32 hour intervals, respectively. The pyridine was then vacuum distilled from the reaction mixture at 1.0 mm Hg pressure. The residue was extracted three times with 200 ml of methylene chloride, and the combined methylene chloride extracts were filtered. The filtrate was concentrated to 100 ml and chromatographed on a column of dry alumina. The column was eluted with methylene chloride followed by 1:1 methylene chloridetetrahydrofuran (THF). The progress of the 2,2'-bis)phenylethynyl) benzidine was followed by means of a 254 nm fluorescent lamp upon irradiation with which the substance afforded an intense blue fluorescence. The portion of eluate containing the 2,2'-bis(phenylethynyl)-benzindine was concentrated to dryness and the residue was dissolved in 250 ml of THF. The substance was precipitated as its bis-HCl salt by the addition of 10 ml of concentrated HCl. The salt was collected by filtration, washed with THF, and suspended in 50 ml of methanol. Addition of 10 ml of concentrated $NH_4OH$ regenerated the free diamine which was precipitated by addition of the methanolic solution to 500 ml of water. The product from the final precipitation was dried under vacuum for 16 hours at 23° C and 1 mm of Hg and dissolved in 100 ml of dry benzene. The benzene solution was concentrated to 50 ml by distillation at atmospheric pressure, and then concentrated to dryness by freeze-drying at 2 microns to give 3.6 g (48 %). The 2,2' -bis (phenylethynyl) benzidine softened above 70° C to a very viscous melt and darkened above 150° C.

Analysis Calc'd for $C_{28}H_{20}N_2$: C,87.50; H,5.21; N,7.29; Found: C,87.46, 87.12; H,5.05, 5.17; N,6.90

Molecular Wt (Mass spectrometry): Calc'd —384; Found —384.

EXAMPLE II 2,2'Bis(phenylethynyl)-5,5'-diaminobipnenyl (B)

a. 2,2'-Bis(acetamido)-5,5'-dinitrobiphenyl (III)

A mixture of 2'-iodo-4'-nitroacetanilide (II) (50.0.2 g, 0.164 mole), copper-bronze (87.9 g) and N,N'-dimethylformamide (350 ml) was stirred and heated at 150° C under nitrogen for 1 hour and filtered. The filter cake was washed with tetrahydrofuran, and the combined filtrate and washings were concentrated under vacuum to 100 ml and poured, with stirring, into 1200 ml of concentrated ammonium hydroxide. The resultant precipitate was filtered, washed with water, and dried at 100° C and 1 mm Hg to yield 34.1 g (58%) of 2,2'-bis-(acetamido)-5,5'-dinitrobiphenyl. An analytical sample, m.p. 263°-265° C, was obtained by recrystallization from ethanol.

Analysis Calc'd for $C_{16}H_{14}N_4O_4$:C,53.60; H,3.91; N,15.63; Found: C,53.60, 53.27; H,3.78, 3.76; N,15.82, 15.74.

Molecular Wt (Mass spectrometry): Calc'd —358; Found —358.

b. 2,2'-Diamino-5,5'-dinitrobiphenyl (IV)

To a solution of 2,2'-bis (acetamido)-5,5'-dinitrobiphenyl (34.1 g, 0.0953 mole) in concentrated sulfuric acid (500 ml) was added, slowly, 250 ml of water. The reaction mixture was stirred and heated at 110° C and 1 mm Hg to give 24.9 g (96 %) of 2,2'-diamino-5,5'-dinitrobiphenyl. An analytical sample, m.p. 315°-317° C, was obtained by recrystallization from ethanol-tetrahydrofuran.

Analysis Calc'd for $C_{12}H_{10}N_4O_4$: C,52.55;
Analysis Calc'd for $C_{16}H_{14}N_4O_4$: C,53.60; H,3.91; N,15.63; Found: C,53.60, 53.27; H,3.78, 3.76; N,15.82, 15.74.

Molecular Wt (Mass spectrometry): Calc'd — 358; Found — 358.

b. 2,2'-Diamino-5,5'-dinitrobiphenyl (IV)

To a solution of 2,2'-bis(acetamido)-5,5'-dinitrobiphenyl (34.1 g, 0.0953 mole) in concentrated sulfuric acid (500 ml) was added, slowly, 250 ml of water. The reaction mixture was stirred and heated at 110° C and 1 mm Hg to give 24.9 g (96%) of 2,2'-diamino-5,5'-dinitrobiphenyl. An analytical sample, m.p. 315°–317° C, was obtained by recrystallization from ethanol-tetrahydrofuran.

Analysis Calc'd for $C_{12}H_{10}N_4O_4$: C,52.55; H,3.68; N,20.43; Found: C,52.31, 52.43; H,3.75, 3.57; N,20.53; 20.64.

Molecular Wt (Mass spectrometry): Calc'd — 274; Found — 274.

c. 2,2'-Diiodo-5,5'-dinitrobiphenyl (V)

A solution of 2,2'-diamino-5,5'-dinitrobiphenyl (24.0 g, 0.0876 mole) in concentrated sulfuric acid (177 ml) was stirred at 0° C while a solution of sodium nitrate (15.3 g, 0.22 mole) in concentrated sulfuric acid (88 ml), precooled to 0° C, was added followed by the slow addition of 85% phosphoric acid (176 ml), after which the ice bath was removed and the reaction mixture was allowed to warm to 23° C while it was stirred for 1 hour.

The dark brown solution was then poured into 1400 ml of ice water, and a cold solution of potassium iodide (146 g, 0.88 mole) in water (550 ml) was added with vigorous stirring. The brown suspension was stirred for 1 hour and then sodium bisulfite (75 g) was added. After an additional 15 minutes of stirring, the reaction mixture was filtered and the filter cake washed with water and dried at 60° C for 12 hours. The dried cake was pyrolyzed at 250° C for 20 minutes, cooled to 50° C and extracted with tetrahydrofuran. The tetrahydrofuran extracts were concentrated and absorbed on alumina. Dry column chromatography with benzene-carbon tetrachloride (1:1) as eluant afforded 17.4 g (40%) of 2,2'-diiodo-5,5'-dinitrobiphenyl, m.p. 230°–232° C, after concentration of the eluate and precipitation by petroleum ether.

Analysis Calc'd for $C_{12}H_6I_2N_2O_4$: C,29.05; H,1.21; I,51.17; N,5.64; Found: C,29.15; H,0.83, 0.90; I,51.72, 51.59; N,5.32, 5.60.

Molecular Wt (Mass spectrometry): Calc'd — 496; Found — 496.

d. 2,2'-Bis(phenylethynyl)-5,5'-dinitrobiphenyl (VI)

A mixture of 2,2'-diiodo-5,5'-dinitrobiphenyl (19.8 g, 0.040 mole), copper phenylacetylide (14.6 g, 0.089 mole) and pyridine (373 ml) was deaerated with nitrogen for 15 minutes and heated at 110° C under nitrogen for 5 hours. The reaction mixture was then cooled to 23° C and poured, with stirring, into 5.5 liters of 10% sulfuric acid. After 1 hour of stirring, the precipitate which formed was filtered, washed with water, dried under suction for 20 hours, and extracted with chloroform. Removal of chloroform and recrystallization from benzene afforded 9.3 g (52%) of 2,2'-bis-(phenylethynyl)-5,5'-dinitrobiphenyl, m.p. 216°–218° C.

Analysis Calc'd for $C_{28}H_{16}N_2O_4$: C,75.66; H,3.63; N,6.30; Found: C,75.82, 75.66; H,3.59, 3.43; N,6.10, 6.07.

Molecular Wt (Mass spectrometry): Calc'd — 444; Found — 444.

e. 2,2'-Bis(phenylethynyl)-5,5'-diaminobiphenyl (B)

A solution of sodium dithionite (8.00, 0.0460 mole) and sodium carbonate (7.01 g, 0.0661 mole) in water (50 ml) was stirred under a nitrogen atmosphere while 2,2'-bis(phenylethynyl)-5,5'-dinitrobiphenyl (0.500 g, 0.00112 mole) was added followed by dioxane (50 ml). The reaction mixture was stirred and refluxed for 2 hours and then the solvent was removed under vacuum. The residue was extracted with benzene and the filtered benzene extracts were freeze-dried to afford 0.198 g (46%) of 2,2'-bis(phenylethynyl)-5,5'-diaminobiphenyl, m.p. 159°–161° C after recrystallization from chloroform-cyclohexane.

Analysis Calc'd for $C_{28}H_{20}N_2$: C,87.47; H,5.24; N,7.29; Found: C,87.07, 87.00; H,5.02, 4.86;N,7.37, 7.38.

Molecular Wt (Mass spectrometry): Calc'd — 384; Found — 384.

EXAMPLE III

Poly[(1,3-dihydro-1,3-dioxo-2H-isoindole-5,2-diyl)[2,2'-bis(phenylethynyl)[1,1'-biphenyl]-5,5'-diyl](1,3-dihydro-1,3-dioxo-2H-isoindole-2,5-diyl)oxy-1,4-phenylenesulfonyl-1,4-phenyleneoxy]

A mixture of 2,2'-bis(phenylethynyl)-5,5'-diaminobiphenyl (0.292 g, 0.76 mmole) and bis [4-(3,4-dicarboxyphenoxy)phenyl]sulfone dianhydride (0.412 g, 0.76 mmole) was dissolved in 250 ml of dried (molecular sieves) N,N'-dimethylacetamide. The reaction mixture was stirred, under an atmosphere of dry nitrogen, at room temperature for 24 hours. Acetic anhydride (10 ml) was added to the reaction mixture which was heated at 130° C for 1.5 hours. The reaction mixture was allowed to cool to room temperature and the polymer isolated by precipitation of the reaction mixture into 2 liters of methanol. The polymer after being washed with methanol, and dried at 80° C for 24 hours exhibited an inherent viscosity (0.5% solution in N,N'-dimethylacetamide at 30° C) of 0.11.

Analysis Calc'd for $(C_{56}H_{30}N_2O_8S)_n$: C,75.50; H,3.39; N,3.14; S,3.60; Found: C,75.55; H,3.25; N,3.05; S,3.40.

Analysis of the polymer by differential scanning calorimetry showed an exothermic reaction maximizing at 237° C. Prior softening of the polymer at 200°–225° C was indicated by both thermomechanical analysis and softening under-load measurements. After curing the polymer at 240°–250° C for 24 hours, a glass transition temperature (Tg) of 350°–360° C was measured by differential scanning calorimetry and softening-under-load.

EXAMPLE IV

Poly[(1,3-dihydro-1,3-dioxo-2H-isoindole-5,2-diyl) [2,2'-bis(phenylethynyl) [1,1-biphenyl]-4,4'-diyl] (1,3-dihydro-1,3-dioxo-2H-isoindole-2,5-diyl)oxy-1,4-phenylenesulfonyl-1,4-phenyleneoxy]

A mixture of 2,2'-bis(phenylethynyl)-4,4'-diaminobiphenyl (1.01 6, 2.63 mmoles) and bis[4-(3,4-dicarboxyphenoxy)phenyl]sulfone dianhydride (1.430 g, 2.63 mmole) was dissolved in 250 ml of N,N'-dimethylacetamide. The reaction mixture was stirred at room temperature, under a nitrogen atmosphere, for 24 hours. Acetic anhydride (10 ml) was then added to the reaction mixture which was heated at 130° C for 1.5 hours. After cooling, the reaction mixture was poured into 2 liters of methanol to precipitate the polymer which was washed with methanol and dried at 80° C for 24 hours. The dried polymer exhibited an inherent viscosity (0.5% solution in N,N'-dimethylacetamide at 30° C) of 0.45.

Analysis Calc'd $(C_{56}H_{30}N_2O_8S)_n$: C,75.50; H, 3.39; N,3.14; S,3.60; Found : C,75.16; H,3.13; N,2.72; S,3.86.

Analysis of the polymer by differential scanning calorimetry showed an exothermic reaction maximizing at 246° C corresponding to the intramolecular cycloaddition of the pendant phenylacetylene groups. No glass transition temperature (Tg) was observed for the polymer below the cycloaddition temperature. After curing the polymer at 240°-250° C for 24 hours, a Tg of 380° C was measured by differential scanning calorimetry.

As seen from the foregoing, the compounds of this invention are useful as monomers for preparing polyimides containing pendant phenylethynyl groups. These groups undergo a thermal intramolecular cycloaddition reaction at temperatures above the softening point of the polyimides. The reaction envolves no volatile by-products, and a modified polymer is provided with no softening point below its decomposition temperature. Thus, the monomers make it possible to provide polyimides which have excellent processing parameters. The polyamides possess a high thermal stability which renders them particularly suitable for use in high temperature applications, such as in the fabrication of fiber reinforced structural composites, fibrous materials, and protective coatings.

As will be evident to those skilled in the art, modification of the present invention can be made in view of the foregoing disclosure without departing from the spirit and scope of the invention.

We claim:

1. A compound selected from the group consisting of 2,2'-bis(phenylethynyl)-4,4'-diaminobiphenyl and 2,2'-bis(phenylethynyl)-5,5'-diaminobiphenyl.

2. The compound of claim 1 which is 2,2'-bis(phenylethynyl)-4,4'-diaminobiphenyl.

3. The compound of claim 1 which is 2,2'-bis(phenylethynyl)-5,5'-diaminobiphenyl.

UNITED STATES PATENT AND TRADEMARK OFFICE
CERTIFICATE OF CORRECTION

PATENT NO. : 4,038,320

DATED : July 26, 1977

INVENTOR(S) : Fred E. Arnold and Frederick L. Hedberg

It is certified that error appears in the above-identified patent and that said Letters Patent are hereby corrected as shown below:

Column 3, line 36, "4:nitroacetanilide" should read -- 4-nitro-acetanilide --. Column 4, line 33, "diaminobipnenyl" should read -- diaminobiphenyl --; line 35, "50.0.2" should read -- 50.02 --; lines 54 to 68, cancel beginning with "b. 2,2'-Diamino-5,5'-dinitrobiphenyl (IV)" to and including "Found - 358." Column 8, line 1, "polyamides" should read -- polyimides --.

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*